United States Patent [19]

Renga et al.

[11] 4,261,906
[45] Apr. 14, 1981

[54] PROCESS FOR MAKING VICINAL EPOXIDES

[75] Inventors: James M. Renga; Albert H. Emmons, both of Midland, Mich.

[73] Assignee: The Dow Chemical Company, Midland, Mich.

[21] Appl. No.: 95,002

[22] Filed: Nov. 16, 1979

[51] Int. Cl.³ .................................................. C07D 301/24
[52] U.S. Cl. .................................. 260/348.16; 260/463
[58] Field of Search ...................................... 260/348.16

[56] References Cited
U.S. PATENT DOCUMENTS 4,069,234  1/1978  Wu .................................. 260/348.16

Primary Examiner—Norma S. Milestone

[57] ABSTRACT

Vicinal epoxides are prepared by decomposing a β-haloalkyl carbonate of the general formula

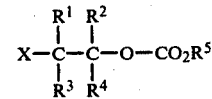

in the presence of a quaternary ammonium or phosphonium salt.

10 Claims, No Drawings

PROCESS FOR MAKING VICINAL EPOXIDES

BACKGROUND OF THE INVENTION

This invention relates to a new process for making vicinal epoxides.

Vicinal epoxides are valuable chemical intermediates and monomers useful in making epoxy adhesives and various heat- and solvent-resistant polymers. A well-known process for making vicinal epoxides from olefins involves the oxidation of the olefinic double bond with aqueous chlorine to form the chlorohydrin and reaction of the chlorohydrin with a base to make the epoxide. However, a major disadvantage of this process is the production of an equivalent of HCl from the aqueous oxychlorination step and another equivalent of inorganic chloride from the reaction of the base with the chlorohydrin intermediate. In the case of epichlorohydrin, the conventional preparation uses the same chemistry with the added initial step of chlorinating propylene to allyl chloride which produces an additional equivalent of HCl.

Ethylene oxide is prepared by oxidizing ethylene with molecular oxygen over a silver catalyst. However, this method is not applicable to other olefins because of low selectivity and the formation of by-products. Another method using oxygen involves oxidizing a hydrocarbon such as isobutane or isopropylbenzene with air to the corresponding tertiary hydroperoxide and then reacting the hydroperoxide with an olefin in the presence of a transition metal catalyst. A disadvantage of this process is the formation of co-product alcohol which must be solid or recycled.

Hydrogen peroxide and peroxy acids are other reagents which have been used to epoxidize olefins. Chemical and economic disadvantages of such methods have precluded their use on a large scale.

It is known that cyclic carbonates can be decomposed to form epoxides in the presence of various catalysts. Such a process particularly directed to the preparation of propylene oxide by decomposition of propylene carbonate in the presence of a sulfonium or phosphonium halide or any of certain metal salts is described in U.S. Pat. No. 4,069,234.

SUMMARY OF THE INVENTION

It has now been found that vicinal epoxides of various kinds, not only the simple alkylene and cycloalkylene oxides, but also their aromatic and halogen-substituted derivatives, can be made in good yield by heating an unsymmetrical β-haloalkyl carbonate of the formula

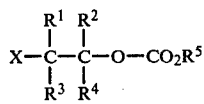

in the presence of a small but effective amount of a quaternary ammonium or phosphonium salt at a temperature of about 25° C.–250° C. The products of this decomposition are $CO_2$, the halide $R^5X$, and the epoxide of the formula

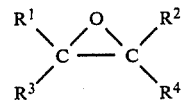

wherein X is Cl or Br, each of $R^1$, $R^2$, $R^3$, and $R^4$ is hydrogen, a hydrocarbon group, $-CH_2X$, or $R^1$ and $R^2$ together form an alkylene group of 3-6 carbon atoms, and $R^5$ is an alkyl group, preferably a lower alkyl group.

DETAILED DESCRIPTION OF THE INVENTION

The term hydrocarbon group as used above to define $R^1$, $R^2$, $R^3$, and $R^4$ includes alkyl groups of one to about 20 carbon atoms, cycloalkyl and alkylcycloalkyl groups of 5-10 carbon atoms, and aromatic hydrocarbon groups of 6-10 carbon atoms. $R^5$ is preferably a lower alkyl group as noted and is most preferably a methyl or ethyl group.

As can be seen from the above description, this process produces two useful products, the alkyl halide $R^5X$ and the epoxide, assuming $CO_2$ to be a waste product. The structure of the starting β-haloalkyl carbonate, therefore, is normally designed to produce not only the desired epoxide, but also a particular useful alkyl halide which has a boiling point sufficiently different from the epoxide to facilitate easy and complete separation of these two products.

The decomposition reaction takes place in the presence of the quaternary salt catalyst at some rate at any temperature from about room temperature to about 250° C., but for normally practical reaction times, the decomposition is preferably carried out at about 150°–250° C. Reaction times can range from 0.001 hour to about 10 hours depending on the structure of the carbonate, the temperature, and the nature and amount of the catalyst.

Substantially any quaternary ammonium or phosphonium salt can catalyze the decomposition reaction. Preferably, these salts have the general formula $R_4AY$ where each R is a hydrocarbon moiety; A is a quaternized nitrogen or phosphorus atom; and Y is an inert (i.e., inert in this process) neutralizing anion which may be inorganic, e.g., chloride, bromide, iodide, bicarbonate, sulfate, or the like; or Y may be an organic ion such as formate, acetate, benzoate, phenate, or bisphenolate. The R groups may be alkyl, aryl, alkaryl, aralkyl, or cycloalkyl. Also, two R groups may combine to form a heterocyclic ring. Illustrative quaternary salt catalysts are tetrabutylammonium bromide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and corresponding ammonium and phosphonium salts with these and other such inorganic and organic neutralizing anions as described above.

Although any significant amount of such a quaternary salt will catalyze the decomposition reaction to some extent, for practical reasons in batch operations, it is preferred to use about 0.1–10 mole percent of the salt based on the carbonate. More quaternary salt catalyst can be used but the excess confers little added advantage and may in fact be disadvantageous.

In a mode of the invention particularly adapted to continuous operation, one or more R groups may be pendant methylene groups from a resin matrix so that the quaternary salt is a salt form of a strong base anion-exchange resin such as DOWEX® 21K, DOWEX® 11, DOWEX® MSA-1, or other such commercially available ion-exchange resins or the phosphonium equivalents of such quaternary ammonium-substituted resins. In such a continuous operation of the process, the β-haloalkyl carbonate starting material is passed at an appropriate flow rate through a bed of the strong base anion resin maintained at a suitable temperature within the limits previously defined.

A reaction solvent or diluent is usually of no advantage and the process is ordinarily run in the absence of such an inert additive. In some cases, however, a solvent may be of some advantage. Inert solvents suitable for use include hydrocarbons such as toluene, xylene, and decane; glycol diethers such as dimethyloxy ethane, substituted amides such as N,N-dimethylformamide, and cyclic compounds such as tetrahydrofuran and sulfolane.

In the preparation of higher boiling epoxides particularly, separation of the epoxide product may be facilitated by running the reaction under appropriately reduced pressure or by passing a stream of nitrogen or other inert gas through or over the reaction mixture.

The β-haloalkyl alkyl carbonate starting materials for this process can be prepared by any of several generally known procedures. Pechukas, U.S. Pat. No. 2,518,058 describes the reaction of an epoxide with a haloformate to make a corresponding β-haloalkyl alkyl carbonate. These mixed carbonate esters can also be made by the acid-catalyzed transesterification reaction of a halohydrin with a dialkyl carbonate. For example, 2-chloroethyl methyl carbonate is produced by the reaction of diemthyl carbonate with ethylene chlorohydrin and 1-chloro-2-propyl ethyl carbonate can be made by reacting diethyl carbonate with 1-chloro-2-propyl alcohol. Variations of this method can be used to make particular halogenated alkyl carbonate esters. Correspondingly monohalo- and dihalopropyl carbonates, for example, can be made by first reacting allyl alcohol with a dialkyl carbonate and then adding hydrogen halide or halogen to the olefinic double bond in the allyl alkyl carbonate product.

EXAMPLE 1

A mixture of 4.57 g of 1-chloro-2-propyl methyl carbonate (contained 20-30 percent of the 2-chloro-1-propyl isomeric ester) and 0.034 g of tetrabutylphosphonium bromide in a 10 ml reaction flask was heated by an oil bath at 180° C.-185° C. for 2 hours. The flask was equipped with a magnetic stirrer, a condenser, and a receiver plus a trap, each of the latter containing 10 g of chloroform cooled to −60° C. After 2 hours of heating, the residue in the reaction flask amounted to 0.23 g of material which contained less than 5 percent starting carbonate. The receiver and trap had gained a total of 2.5 g of reaction products which were determined by nuclear magnetic resonance spectroscopic and chromatographic analysis to be a mixture of propylene oxide and methyl chloride, some methyl chloride having been lost because of its high volatility. The conversion of chloropropyl methyl carbonate was nearly 100 percent and the analyses indicated a yield of about 95 percent of the theoretical for propylene oxide.

EXAMPLES 2–3

The procedure of Example 1 was repeated twice using 0.027 g of tetrabutylammonium chloride and 0.037 g of tetrabutylammonium iodide respectively in place of the phosphonium salt catalyst. In each case, the yield of propylene oxide was 97–99 percent of the theoretical amount but the conversion of starting carbonate was relatively low, about 20 percent and 25 percent respectively.

EXAMPLE 4

The procedure of the above examples was repeated using 0.5 g of DOWEX® MSA-1 ion-exchange resin as the catalyst. The resin contained 40–50 percent water. This resin is a strong base anion resin consisting of a macroporous cross-linked styrene polymer matrix having pendant quaternary ammonium chloride functionalities. After 2.5 hours of heating time, about 99 percent of the carbonate had been decomposed to form 95 percent of the theoretical quantity of propylene oxide.

EXAMPLES 5–11

Other alkyl 1-chloro-2-propyl carbonates (containing 20–30 percent of the corresponding 2-chloro-1-propyl ester) were heated for 2 hours as described above to produce propylene oxide using different tetrabutylphosphonium salts as catalysts. Each carbonate was used in a quantity of 0.03 g mole. The results are summarized in Table I.

TABLE I

| Example No. | Alkyl group | Phosphonium Catalyst Salt | Wt. g. | % Conv. | % Sel. |
|---|---|---|---|---|---|
| 5 | ethyl | bromide | 0.034 | 2–3 | 99 |
| 6 | ethyl | bicarbonate | 0.032 | 5–6 | 99 |
| 7 | ethyl | formate | 0.030 | 35–37 | 99 |
| 8 | ethyl | bisphenate[b] | 0.075 | 37–38 | 99 |
| 9 | ethyl | bisphenate[b] | 0.215 | 98 | 96 |
| 10[a] | n-propyl | bisphenate[b] | 0.215 | 99 | 95 |
| 11[a] | isopropyl | bisphenate[b] | 0.215 | 39 | 93 |

[a]Heating time was 6 hours.
[b]Monosalt of Bisphenol A complexed with one molecule of the free bisphenol.

EXAMPLE 12

A mixture of 4.16 g of 2-chloroethyl methyl carbonate and 0.034 g of tetrabutylphosphonium bromide was heated at 180° C. for 3 hours in the apparatus previously described. A carbonate conversion of 99.7 percent was obtained with an 89 percent yield of ethylene oxide.

EXAMPLE 13

In the same way, a mixture of 5.49 g of 2-bromoethyl methyl carbonate and 0.034 g of tetrabutylphosphonium bromide was heated for 6 hours at 200° C. to produce a carbonate conversion of 100 percent and an 88 percent selectivity to ethylene oxide and methyl bromide.

EXAMPLE 14

Similarly, a mixture of 2.92 g of 1-chloro-2-hexyl methyl carbonate (containing 22 percent of the 2-chloro-1-hexyl isomer) and 0.024 g of tetrabutylphosphonium formate was heated at 200° C.–205° C. for 2 hours to produce an isolated yield of 98 percent of the theoretical quantity of 1,2-epoxyhexane.

EXAMPLE 15

A mixture of 3.34 g of 1-chloro-2-octyl methyl carbonate (containing 21 percent of the corresponding 2-chloro-1-octyl ester) and 0.024 g of tetrabutylphosphonium formate was heated as above at 200° C.–205° C. for 2 hours at reduced pressure (200 mm Hg). An isolated yield of 96 percent of theory of 1,2-epoxyoctane was collected in the receiver.

EXAMPLE 16

A mixture of 2.89 g of 2-chlorocyclohexyl methyl carbonate and 0.039 g of tetrabutylphosphonium salt of Bisphenol A (as used in Examples 8–11) was heated at 200° C.–205° C. for 1.5 hours. A yield of 1.34 g of 1,2-epoxycyclohexane was collected in the receiver.

EXAMPLE 17

In a procedure similar to that used in Example 15, a mixture of 3.89 g of 2-bromo-1-phenylethyl methyl carbonate and 0.024 g of tetrabutylphosphonium formate was heated at 180° C. for 2 hours at 50 mm Hg absolute pressure. The product condensed in the receiver was 1.58 g of a mixture containing 40 percent styrene oxide and 60 percent phenylacetaldehyde.

EXAMPLE 18

The reduced pressure technique of Examples 15 and 17 was followed in heating a mixture of 5.61 g of 1,3-dichloro-2-propyl methyl carbonate and 0.078 g of the tetrabutylphosphonium Bisphenol A salt used in Examples 8–11 and 16. After 2 hours at 195° C.–200° C. and 100 mm Hg absolute pressure, 2.85 g of 88 percent pure epichlorohydrin had condensed in the receiver.

EXAMPLE 19

To a 4-neck 50 ml reaction flask equipped with a mechanical stirrer, addition funnel, distillation head, and nitrogen inlet there was added 0.24 g of tetrabutylphosphonium formate and the flask was heated to 185° C.–190° C. with a stream of 30 ml/min. of nitrogen passing through while 2.81 g of 2,3-dichloro-1-propyl methyl carbonate was added over a period of 30 minutes. Analyses of 1.4 g of condensed effluent in the receiver cooled by solid $CO_2$ and 0.47 g of residue indicated a 90–95 percent conversion of carbonate with a 50–60 percent yield of epichlorohydrin.

We claim:

1. A process for making a vicinal epoxide of the formula

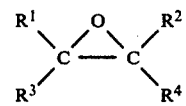

which comprises contacting a carbonate ester of the formula

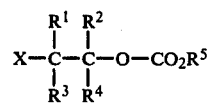

wherein $R^1$, $R^2$, $R^3$, and $R^4$ are individually hydrogen, a hydrocarbon group, $-CH_2X$, or $R^1$ and $R^2$ together form an alkylene group of 3-6 carbon atoms, $R^5$ is an alkyl group, and X is Cl or Br, with a quaternary ammonium or phosphonium salt catalyst at about 25° C.–250° C. and separating said epoxide from the ester-salt reaction mixture.

2. The process of claim 1 wherein the temperature is about 150° C.–250° C.

3. The process of claim 2 wherein $R^3$ and $R^4$ are hydrogen and $R^5$ is a lower alkyl group.

4. The process of claim 3 wherein one of $R^1$ and $R^2$ is a methyl group and the other is hydrogen and the epoxide product is propylene oxide.

5. The process of claim 3 wherein one of $R^1$ and $R^2$ is a chloromethyl group and the other is hydrogen and the epoxide product is epichlorohydrin.

6. The process of claim 3 wherein $R^1$ is hydrogen, $R^2$ is a phenyl group, and the epoxide product is styrene oxide.

7. The process of claim 3 wherein $R^1$ and $R^2$ together form a tetramethylene group and the epoxide product is cyclohexene oxide.

8. The process of claim 3 wherein one of $R^1$ and $R^2$ is a butyl group and the other is hydrogen and the epoxide product is 1,2-epoxyhexane.

9. The process of claim 3 wherein one of $R^1$ and $R^2$ is a hexyl group and the other is hydrogen and the epoxide product is 1,2-epoxyoctane.

10. The process of claim 2 wherein the salt catalyst is a strong base anion-exchange resin having quaternary ammonium haldide functionalities.

* * * * *